United States Patent

Reynaud et al.

[11] Patent Number: 5,890,904
[45] Date of Patent: Apr. 6, 1999

[54] RADIO-OPAQUE TOOTH POST MADE OF COMPOSITE MATERIAL

[75] Inventors: Marc Reynaud, 23, avenue Plaine Fleurie, 38240- Meylan; Pierre-Luc Reynaud, 9, rue du Rif-Tronchard, 38120- Saint-Egreve; Manh Chu, Saint-Egreve, all of France

[73] Assignees: Marc Reynaud, Meylan; Pierre-Luc Reynaud, Saint-Egreve, both of France

[21] Appl. No.: 894,436

[22] PCT Filed: Mar. 1, 1996

[86] PCT No.: PCT/FR96/00329

§ 371 Date: Aug. 20, 1997

§ 102(e) Date: Aug. 20, 1997

[87] PCT Pub. No.: WO96/26686

PCT Pub. Date: Sep. 6, 1996

[30] Foreign Application Priority Data

Mar. 1, 1995 [FR] France .................................. 95 02363

[51] Int. Cl.⁶ ........................................................ A61C 5/08
[52] U.S. Cl. .............................................................. 433/220
[58] Field of Search ....................................... 433/220, 221

[56] References Cited

U.S. PATENT DOCUMENTS

| | | | |
|---|---|---|---|
| 1,649,508 | 11/1927 | Carmichael | 433/224 |
| 5,074,792 | 12/1991 | Bernadat | 433/220 |
| 5,328,372 | 7/1994 | Reynaud et al. | 433/220 |
| 5,518,399 | 5/1996 | Sicurelli, Jr. et al. | 433/220 |
| 5,564,929 | 10/1996 | Alpert | 433/220 |

FOREIGN PATENT DOCUMENTS

| | | |
|---|---|---|
| 0 385 892 | 9/1990 | European Pat. Off. . |
| 0 432 001 | 6/1991 | European Pat. Off. . |
| 2 588 181 | 4/1987 | France . |
| 2 626 167 | 7/1989 | France . |

*Primary Examiner*—John J. Wilson
*Attorney, Agent, or Firm*—Young & Thompson

[57] ABSTRACT

A tooth post made of composite material includes a central core (3) made of a resin matrix wherein are embedded fibers (5) which give the post (1) its main mechanical properties. The central core (3) is wrapped in a sheath (6) consisting of at least one layer of fiber (7) made of radio-opaque material.

10 Claims, 1 Drawing Sheet

RADIO-OPAQUE TOOTH POST MADE OF COMPOSITE MATERIAL

The present invention relates to a tooth post made of composite material presenting an opacity allowing easy location thereof by radiography.

It is known that, in the dental art, in order to strengthen a tooth, posts are employed which are mostly made of metal. Although these posts are easily locatable by the conventional means of radiography, they nonetheless present the drawback of presenting moduli of elasticity very different from those of the teeth in which they are fixed, so that they tend, during use, to injure the dentin, thus bringing about their release after a more or less long time.

In order to avoid this drawback, it has been proposed to employ posts made of composite materials of which the moduli of elasticity are close to those of the dentin, so that they preserve the latter, consequently ensuring a long-lasting hold of the post.

Such posts are mostly constituted by elements transparent to X-rays, so that they are difficult to locate, which is deterimental, on the one hand, from the medical standpoint, particularly in the case of an accidental ingestion, and on the other hand, from the administrative standpoint if it is desired to prove that these posts have been positioned.

It is, of course, possible, in order to ensure opacity of a post, to incorporate in the resin of which it is constituted, radio-opaque fillers which one attempts to distribute regularly in its mass. Now, it has been ascertained that, even when these fillers were relatively well distributed, the contour of the post obtained in X-radiography was not perfectly defined, particularly when the outer face of the post had undergone a specific machining. In order to avoid this drawback, a solution would be to increase the quantity of the fillers used. However, it has been ascertained that, in order to obtain a post whose contour under X radiography is perfectly defined, it was necessary to add a quantity of fillers such that the mechanical qualities of the post were then reduced.

It is an object of the present invention to propose a means for making a tooth post whose contour, obtained under X-radiography, is perfectly defined without its mechanical qualities being reduced.

The present invention thus has for its object a tooth post made of composite material, characterized in that it comprises a central core constituted by a matrix of hardenable resin in which are embedded fibers which give the post its main mechanical qualities, this central core being surrounded by a sheath constituted by at least one layer of fibers made of a radio-opaque material.

The fibers constituting the sheath may preferably be constituted by continuous fibers which extend substantially from one end of the post to the other. Furthermore, the fibers of the central core may be constituted by fibers transparent to X-rays.

In one embodiment of the invention, the peripheral sheath is constituted by at least two layers of intersecting fibers.

The fibers constituting the peripheral sheath are advantageously fibers of silica, ceramics, silicon carbide, or glass fibers with a high content of calcium oxide.

An embodiment of the present invention will be described hereinafter by way of non-limiting example, with reference to the accompanying drawings, in which.

Figure 2:
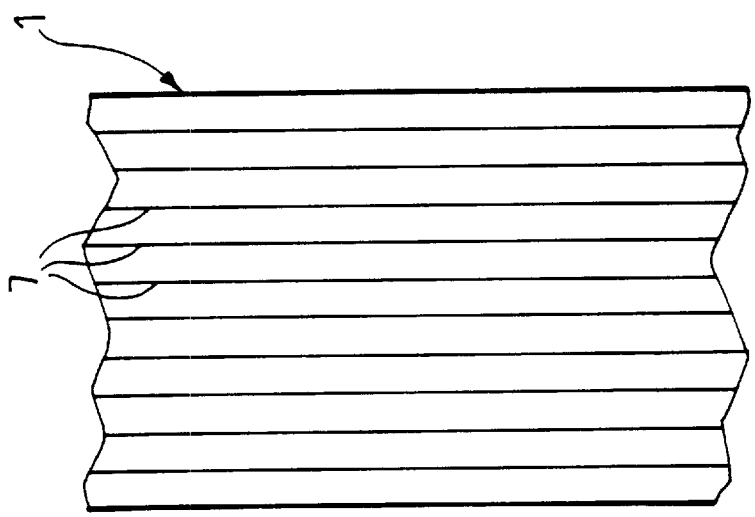
FIG. 2 is an enlarged partial view in elevation of the post shown in FIG. 1.
Figure 1:
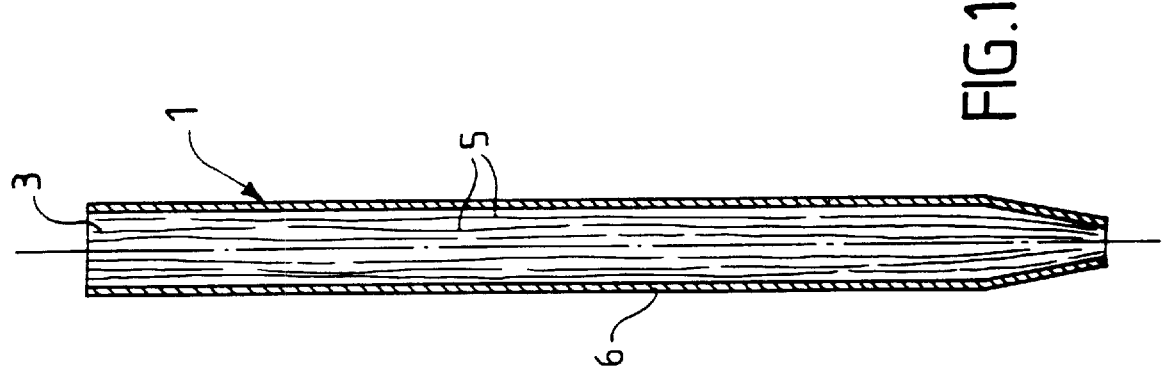
FIG. 1 is a view in axial and longitudinal section of a post according to the invention.

FIGS. 1 and 2 show a tooth post 1 comprising a central core 3 formed by a matrix of epoxy resin in which are embedded fibers transparent to X-rays such as glass fibers 5 which extend over the whole length of the post 1. The nature of these fibers, their diameter and their quality are determined by the mechanical qualities that it is desired to give the post 1.

The periphery of the post comprises a sheath 6 formed by a layer of radio-opaque fibers 7 which are disposed longitudinally over the whole length of the post 1.

These fibers 7 are preferably isotropic fibers, which enables them to modify only slightly by their presence the transverse and longitudinal moduli of elasticity given to the post 1 by the core 3 thereof. Preferably, and for the same reason, the modulus of elasticity of these fibers 7 is as low as possible. As for their refractive index, it is as high as possible. The thickness of the peripheral sheath 6 extends over one or more layers and is particularly small having regard to the overall thickness of the post 1.

In order to constitute the sheath 6, ceramic fibers may thus be employed, which have isotropic properties and of which the longitudinal and transverse moduli of elasticity are of the order of 186 GPa and of which the refractive index is of the order of 1.62.

Silicon carbide fibers may also be employed, whose modulus of elasticity is close to that of the ceramic fibers, but which present a refractive index greater than 2. Such fibers can be used in a lesser quantity, for equal opacity, which makes it possible to minimize their influence on the transverse and longitudinal moduli of elasticity of the post 1.

It has been ascertained that the dental post in accordance with the invention presented on the X-radiographies a perfectly defined contour, which, on the one hand, enabled their precise positioning with respect to the tooth to be defined, but also their specific shape to be defined.

The fibers 7 constituting the peripheral sheath 6 may be contiguous, but it is, of course, possible, according to the invention, to constitute a peripheral sheath by means of non-contiguous fibers possibly coming into contact with one another at points.

Figure 3:
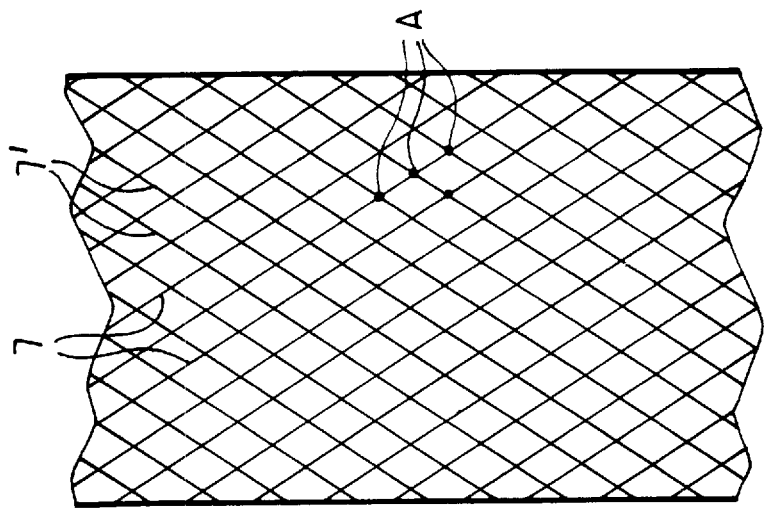
FIG. 3 is an enlarged partial view in elevation of a variant embodiment of a post according to the invention.

In an embodiment of the invention shown in FIG. 3, the peripheral sheath 6 is thus constituted by two superposed and intersecting layers of fibers 7 and 7', which are helically wound on the periphery of the post 1. Such an arrangement makes it possible to obtain a regular distribution over the whole outer surface of the post, of points of greater opacity corresponding to the points of intersection A of fibers 7 and 7'. The regular distribution obtained on the periphery of the post 1 makes it possible clearly to define the radiographic contour thereof.

According to the invention, the central elements constituting the core of the post 1 and in particular the nature, quantity and distribution of the fibers, are used to give the post the desired mechanical qualities and in particular the longitudinal and transverse moduli of elasticity. The radio-opaque fibers disposed on the periphery may be such that they have the least possible influence on the mechanical characteristics of the post, so that their sole role is to control the radio-opacity of the post.

In order to constitute the sheath 6, glass fibers with a high rate of calcium oxide, of the order of 17% to 25% by weight, may also be used, such as those marketed by the firm OWENS CORNING FIBERGLASS under the Trademark "ECR GLASS".

These fibers present the advantage of possessing a high refractive index, of the order of 1.58, as well as an excellent corrosion resistance. These fibers, while moreover using high-resistance glass fibers to constitute the central core, make it possible to produce a dental post of great homogeneity.

Furthermore, by reason of their colour, these fibers are particularly interesting from the aesthetic standpoint.

We claim:

1. Tooth post made of composite material, characterized in that it comprises a central core (3) constituted by a matrix of hardenable resin in which are embedded fibers (5) which give the post (1) its main mechanical qualities, this central core (3) being surrounded by a sheath (6) constituted by at least one layer of fibers (7) made of a radio-opaque material.

2. The post according to claim 1, characterized in that the sheath is constituted by continuous fibers which extend substantially from one end of the post to the other.

3. The post according to claim 1, characterized in that the fibers of the central core are transparent to X-rays.

4. The post according to claim 1, characterized in that the peripheral sheath (6) is constituted by at least two intersecting layers of fibers (7).

5. The post according to claim 1, characterized in that the peripheral sheath (6) is constituted by at least one layer of fibers oriented in the same direction as the central fibers.

6. The post according to claim 1, characterized in that the fibers constituting the peripheral sheath (6) are silicon carbide fibers.

7. The post according to claim 1, characterized in that the fibers constituting the peripheral sheath (6) are silica fibers.

8. The post according to claim 1, characterized in that the fibers constituting the peripheral sheath (6) are ceramic fibers.

9. The post according to claim 1, characterized in that the fibers constituting the peripheral sheath (6) are glass fibers with a high proportion of calcium oxide.

10. The post according to claim 9, characterized in that the glass fibers contain between 15% and 30% by weight of calcium oxide.

* * * * *